United States Patent [19]

Jenkins et al.

[11] 4,440,550
[45] Apr. 3, 1984

[54] ON-COLUMN INJECTOR

[75] Inventors: Rand G. Jenkins, Roseville; Norman W. Wohlers, Davis, both of Calif.

[73] Assignee: J & W Scientific, Inc., Rancho Cordova, Calif.

[21] Appl. No.: 508,742

[22] Filed: Jun. 28, 1983

[51] Int. Cl.³ .............................................. B01D 15/08
[52] U.S. Cl. .......................................... 55/67; 55/197; 55/386
[58] Field of Search ............... 210/67, 197, 386, 198.2

[56] References Cited

U.S. PATENT DOCUMENTS

| 4,228,008 | 10/1980 | Karol et al. | 55/197 X |
| 4,269,608 | 5/1981 | Sisti et al. | 55/67 |
| 4,383,839 | 5/1983 | Sisti et al. | 55/67 |

Primary Examiner—John Adee
Attorney, Agent, or Firm—Townsend & Townsend

[57] ABSTRACT

An apparatus and method for injecting samples into capillary-type gas chromatographic columns allows a portion of the column to be withdrawn from the chromatograph oven prior to injection. The sample is injected into the withdrawn portion of the column which is then inserted back into the oven to initiate volatilization. The apparatus includes a syringe holder which is attached to the inlet end of the column and a collapsible support mechanism for extending the syringe holder away from the chromatograph oven. The sample is injected into the column while the support is extended away from the oven. After the injection is completed, the support is collapsed causing the portion of the column carrying the sample to be abruptly introduced into the oven.

10 Claims, 3 Drawing Figures

ON-COLUMN INJECTOR

BACKGROUND OF THE INVENTION

1. Field of the Invention

The present invention relates generally to a method and apparatus for injecting a liquid sample into a gas chromatograph, and more particularly to the on-column injection of such a sample into a capillary column.

2. Description of the Prior Art

Gas chromatography provides for the separation and quantitative determination of gases, volatile liquids, and solids. The separation is carried out in a column which comprises the fixed or immobile phase. The immobile phase may be a column packing, such an as inert solid support coated with a non-volatile stationary liquid. The stationary liquid is chosen to be non-volatile at the column temperature and to provide the proper interaction with the materials being selected. For example, relatively polar liquid phases are chosen for the selection of polar solutes, while non-polar liquid phases are used to separate relatively non-polar solutes. More recently, very high efficiency separation has been achieved with glass, typically fused silica, capillary tube columns having inside diameters of from about 0.007 to 0.020 inches where the stationary liquid phase is coated directly on the inside of the capillary tube.

Chromatographic separation is carried out by injecting the sample to be analyzed into a carrier gas stream flowing through the column. The solutes are selectively adsorbed into and evaporated from the stationary phase, resulting in a differential rate of migration through the column for different species. The species are identified by their characteristic transit time through the column. A detector, such as a thermal conductivity detector, a flame ionization detector, or a spectrometer, is located at the outlet of the column for detecting the emergence of the species over time.

In the case of gas chromatographic analysis of liquid samples, it is necessary to maintain the column at an elevated temperature (so that the liquid sample exhibits sufficient vapor pressure to pass through the column by repeatedly and alternately diffusing into the gas phase and dissolving in the liquid phase). A variety of techniques may be used for vaporization of the liquid sample prior to, or simultaneous with, injection into the column. Conventionally, a pre-heater, or injection-port flash vaporizer, heats the sample to a temperature so that the sample vaporizes rapidly when injected into a stream of heated carrier gas. When the major part of the sample volume which has been vaporized in this manner is directed to the column, the technique is referred to as "splitless" injection. Frequently, because of the limited capability of capillary columns to handle high volume sample concentrations (such as with neat or undiluted materials), it is necessary to inject only a portion of the vaporized sample into the column. This is known as split injection. Such split injection can result in a discriminatory separation of the components in the sample upon vaporization, causing inaccurate determination.

To allow the direct injection of small sample sizes, on the order of 0.1 to 2 $\mu l$, various on-column injection techniques have been developed. Much of the early work in this field was done by Grob and Grob, Jr. and is reported in a series of articles. See, e.g., Grob et al. (1974) J. Chromatography 94:53-64; Grob et al. (1978) J. Resol. Chromatography 1:57-64; Grob et al. (1978) J. Chromatography 151:311-320; Grob (1978) J. Resol. Chromatography 1:263-267; and Grob et al. (1979) J. Resol. Chromatography 2:109-117.

The on-column injection method of Grob and his coworkers utilizes a lengthy, narrow syringe needle which allows injection of the samples into the column at a point within the chromatograph oven. In this way, the sample can be vaporized directly as it is injected into the column. Such direct injection of a liquid into a column heated above the solvent boiling point, however, can create problems. First, the solvent will rapidly vaporize causing the more volatile components to be lost as they are pushed by the pressure pulse backward past the needle and out of the column. Moreover, less volatile components may remain in the needle because of the pre-volatilization of the solvent and its rapid loss from the needle. Even if the user attempts to inject the sample slowly in an attempt to minimize the pressure pulse caused by the temperature gradient, capillary forces will draw the sample along the needle resulting in the loss of less volatile components. See Galli et al. (1981) J. Chromatography 203:193-2.5. Finally, the distributed volatilization of the sample over the period of the injection causes band broadening since those portions of the sample which are first injected have a lead over the remaining portions in reaching the detector end of the column.

In an attempt to overcome these problems, it has been proposed to cool the initial length of the chromatographic column in the oven by directing a stream of cooled air alongside. This technique is described in U.S. Pat. No. 4,269,608 to Sisti et al. Such secondary cooling, however, is not completely effective due to the low heat capacity of the coolant, the rapid mixing of the cooled air within the heated oven, and the low thermal mass of the fused silica columns. Moreover, such cooling can result in a loss of component resolution because the moving sample must ascend a positive temperature ramp.

Thus, it would be desirable to provide an improved method and device for injecting liquid and other samples into capillary columns used in gas chromatography.

SUMMARY OF THE INVENTION

The present invention provides an improved method and apparatus for injecting samples to be analyzed into chromatographic capillary columns maintained in ovens. By maintaining an initial portion of the capillary column outside of the chromatographic oven while the sample is being injected, the sample enters the column under ambient conditions and the problems associated with flashing, pre-volatilization, plug flow, and the like are minimized. After the sample is injected into the initial portion of the column, the column can be abruptly inserted back into the oven so that the entire sample (which has spread over a finite length of column) is heated and volatilized substantially instantaneously. Such uniform volatilization in turn reduces the band broadening heretofore associated with on-column type injectors.

The apparatus comprises a syringe holder which is collapsibly mounted on the chromatograph oven so that the holder can be moved toward and away from the oven. The inlet end of the chromatographic column (which is typically flexible fused silica) is brought out from the oven through an orifice and attached to one end of the syringe holder. The syringe holder, in turn, has a central bore which communicates with the inlet end of the capillary and which allows the user to insert a syringe needle through the holder and into the column. The syringe holder further includes a carrier gas inlet for continuously providing a flow of carrier gas into the column, and a mechanism for sealing the central bore from the outside when the syringe needle is withdrawn. Thus, the user is able to extend the syringe holder upward from the chromatograph oven prior to injection of the sample. After turning on the carrier gas flow, the sealing mechanism is opened and the syringe inserted through the bore so that the syringe tip enters the inlet end of the column. The sample is then injected, the syringe withdrawn, and the central bore sealed. The syringe holder is then abruptly lowered to insert the capillary tubing back into the oven to provide the benefits described above.

DESCRIPTION OF THE PREFERRED EMBODIMENT

Figure 1:
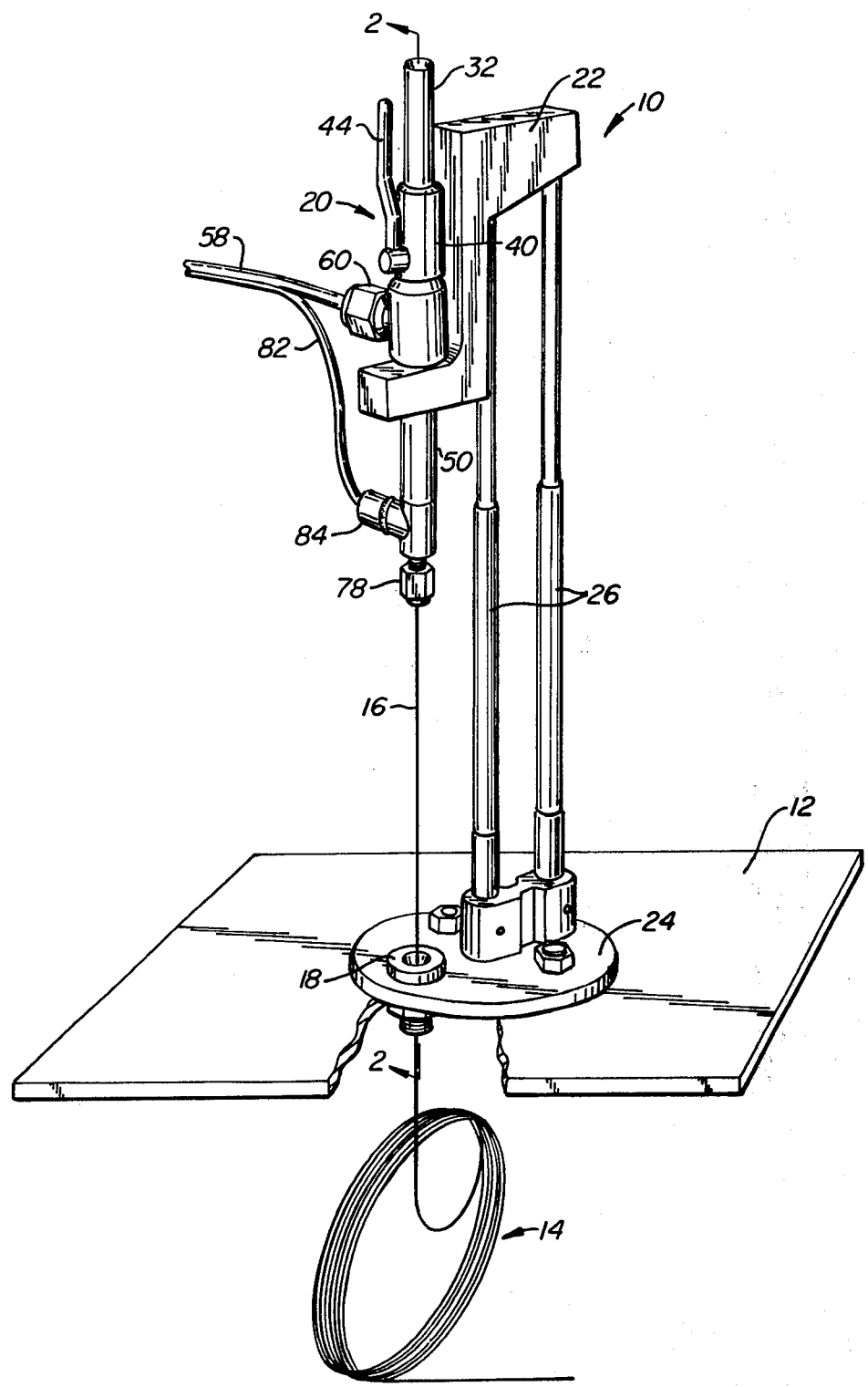
FIG. 1 is a perspective view of the on-column injector of the present invention.

FIG. 1 illustrates an on-column injector 10 constructed according to the principles of the present invention. The injector 10 is mounted on a chromatograph oven 12, only a portion of which is shown. A flexible capillary column 14 is located within the oven 12 and is typically coiled to conserve space. An inlet end 16 of the column 14 is drawn upward through a fitting 18 in the wall of the oven 12. As will be described in detail hereinafter, the fitting 18 allows the inlet end 16 of the column 14 to slide freely in and out of the interior of the oven 12.

The on-column injector 10 comprises a syringe holder 20 mounted on a bracket 22. The bracket 22 is supported above a baseplate 24 on a pair of telescopic columns 26. The syringe holder 20 is aligned with the fitting 18 so that the inlet end 16 of the capillary column 14 may be attached thereto. In this way, the bracket 22 may be raised and lowered on the telescopic columns 26 in order to withdraw and insert the inlet end 16 of the column 14 from the interior of the oven 12.

Figure 2:
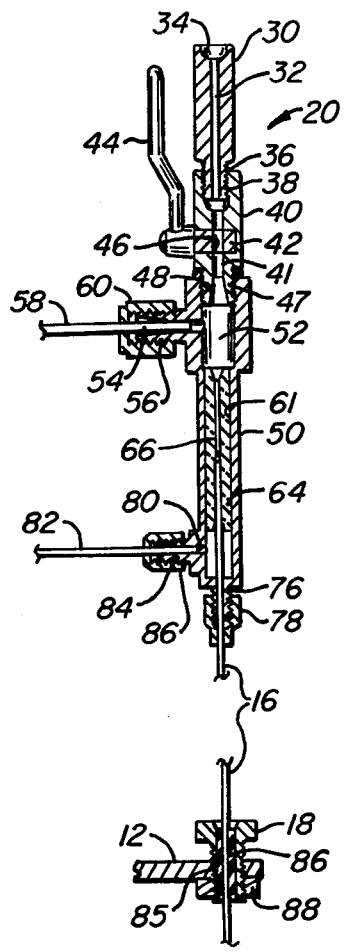
FIG. 2 is a sectional view taken along line 2—2 in FIG. 1.
Figure 3:
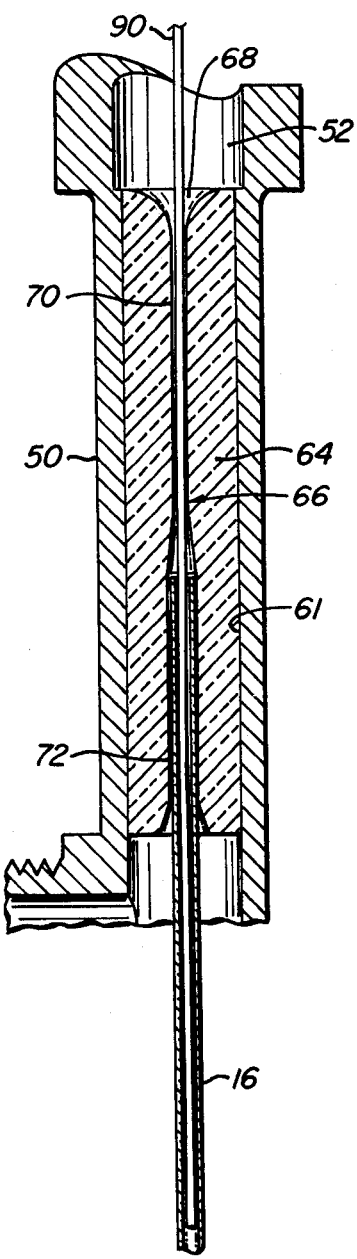
FIG. 3 is an enlarged sectional view of a portion of FIG. 2 illustrating the insertion of the syringe needle into the capillary column.

Referring now to FIGS. 2 and 3, the construction of the syringe holder 20 will be described in greater detail. The syringe holder 20 includes a glass restrictor tube 30 having an axial bore 32 therethrough. The restrictor tube 30 terminates at one end in a concave receptacle 34 which helps guide the syringe needle into the bore 32. The opposite end 36 of the restrictor tube 30 is threaded.

The threaded end 36 of the restrictor tube 30 is received in a female threaded connector 38 formed at one end of a stop cock 40. The stop cock 40 includes an axial passage 41 having a plug 42 which is rotated by handle 44 in the conventional manner. When the handle 44 is aligned with the axis of the syringe holder 20 as illustrated in FIG. 2, an opening 46 of the plug 42 is in line with the axial passage 41 of the stop cock. When the handle 44 is not so aligned, the axial passage 41 is blocked and the inlet end 16 of the capillary column 14 is sealed from the surroundings.

The stop cock 40 is connected to an injector body 50. The stop cock 40 includes a male threaded connector 47 at its lower (as viewed in the Drawings) end, which connector is received in a female threaded connector 48 at the upper end of the injector body 50. The upper end of the injector body 50 also includes a plenum 52 having a side inlet passage 54 formed in threaded nipple 56. The opening 54 is connected to a flexible carrier gas line 58 using a conventional compression fitting 60.

A glass aligning tube 64 is mounted within an axial passage 61 formed in the injector body 50, as best illustrated in FIG. 3. The aligning tube 64, in turn, includes an axial bore 66 which, when the aligning tube 64 is in place, is aligned with axial bore 32 through the restrictor tube 30 and axial passage 41 through the stop cock 40. At one end, the axial bore 66 terminates in a flared opening 68. The flared opening 68 has a decreasing diameter in the downward direction until reaching a minimum inside diameter which remains constant through a first section 70 of the axial bore 66. About half-way through the aligning tube 64 (in the axial direction) the axial bore 66 flares slightly and the remaining portion 72 has a somewhat larger diameter. By properly selecting the inside diameter of the second section 72, the inlet end 16 of the capillary column 14 can be inserted into the second section up until the point where it narrows.

The inside diameter of the second section 72 will be slightly larger than the outside diameter of the capillary tube in use. For common capillaries having outside diameters of 0.40 mm and 0.50 mm, inside diameters of 0.25 mm and 0.33 mm, respectively, are suitable. The inside diameter of the first section 70 of the axial bore 66 will be slightly larger than the outside diameter of the syringe needle being used. Most commonly, for syringe needles having a diameter of 0.19 mm, a diameter of 0.245 mm is suitable. For different size syringe needles and/or capillary tubes, aligning tubes 64 having the appropriate diameters for the first and second sections 70, 72 of the axial bore 66 can be inserted into the injector body 50.

Referring back to FIG. 2, the capillary tube 16 is inserted through a threaded nipple 76 at the lower end of the injector body 50 and is held in place by a compression fitting 78. A purge port 80 is provided near the bottom of the injector body 50 to allow withdrawal of a purge stream of the carrier gas. A flexible purge line 82 is connected to the purge port 80 through a threaded nipple 84 and compression fitting 86 in a conventional manner. The size of the purge port is selected to pass approximately 60 to 90% of the carrier gas entering through line 58. The constant purge allows a higher inlet flow of carrier gas which is easier to regulate, as will be described in more detail hereinafter.

Fitting 18 is secured in a threaded opening 85 tapped in the wall of chromatograph oven 12. The fitting 18 includes a graphite bearing 86 for receiving the inlet end 16 of the capillary 14 and allowing it to move freely in the axial direction. The fitting 18 is held in place by a nut 88.

Use of the injector 10 for introducing a sample to be analyzed into a capillary column will now be described. The description will be made in reference to a liquid sample where the invention is used to a maximum advantage. The injector 10, however, can be used for introducing gaseous samples as well and there is no intent to limit the invention to a particular type of sample.

Prior to introducing the sample, the inlet end 16 of the capillary column 14 will be withdrawn from the oven 12 by raising the bracket 22. The length of column which must be withdrawn depends on the volume of sample to be introduced and on the internal diameter of the capillary column. As the sample is injected from the syringe needle, it will spread axially on the inside wall of the column over a finite length. For example, a 1 $\mu$l sample injected into a column having an inside diameter of 0.25 mm will spread over a section of column approximately 10 cm in length. For such a sample, it will be desirable to withdraw at least 10 cm of the column.

After an appropriate length of the inlet 16 has been withdrawn and the chromatograph oven has reached its operating temperature, the stop cock 40 should be closed and the flow of carrier gas through line 58 initiated. The selection of carrier gas is conventional and will typically be hydrogen, helium, or nitrogen, depending on the particular application. The carrier gas pressure is chosen to provide a desired flow rate of carrier gas through the column 14. Such flow rate is typically very low, in the range from about 1 to 3 ml/min, and is difficult to regulate. For a given flow rate, the inlet pressure will be inversely related to the column diameter and directly related to the column length. Also, the amount of carrier gas purged through line 82 will reduce the flow through column 14. For example, a column having a diameter of 0.32 mm, a length of 15 meters and a purge of about 75% will require a relatively low carrier gas pressure of about 2 psig to pass 2 ml/min, while a column having a diameter of 0.25 mm and a length of 100 meters will require a relatively high inlet pressure of about 60 psig to pass the same volume.

After initiating carrier gas flow, the sample to be analyzed is drawn into the syringe. The sample may be a liquid (either with or without an added solvent), a solid dissolved or suspended in a solvent, or a gas. The injector will function with virtually any sample capable of on-column injection into a capillary column.

To introduce the syringe needle into the inlet end 16 of the column 14, the stop cock 40 is opened by turning the handle 44 into alignment with the syringe holder 20. The syringe needle (illustrated at reference number 90 in FIG. 3) should be inserted into the galss restrictor tube 30 prior to opening the stop cock 40. When the stop cock is opened, the user will be able to sense the interior gas pressure exerted against the syringe needle. The needle should then be slowly inserted downward through the plug 46 and into the plenum 52. The axial bore 32 of the restrictor tube is directed so that the needle 90 will enter the flared opening 68 of the glass aligning tube 64 as it is further inserted downward. As the needle emerges from the first section 70 of the aligning tube 64, it will enter the open end of the inlet 16 of the capillary column 14, as illustrated in FIG. 3. The needle 90 should be inserted downward until it is visible in the column 14 at a point approximately 1 or 2 cm below the bottom of the syringe holder 20. In the configuration in FIG. 3, the carrier gas will flow through the annular space between the outside of the syringe needle and the inside of the first portion 70 of the axial bore 66 to enter the inlet 16 of the capillary column 12. The user is now ready to inject the sample from the syringe into the column inlet.

For small sample sizes of 1 $\mu$l and below, the sample may be rapidly injected from the syringe into the inlet 16 of the column 14. For larger sample sizes, the injection should be somewhat slower to avoid forming a plug of liquid in the column. A liquid plug can form a barrier across the capillary, preventing the flow of carrier gas past the liquid and causing the plug to be blown down the column by the carrier gas. For samples in the range from 1 to 2 $\mu$l, injection over several seconds is preferred. For sample sizes larger than 2 $\mu$l, an injection time of from about 5 to 10 seconds is usually suitable.

After the sample has been injected, the needle should be withdrawn to a point above the stop cock, the stop cock closed, and the needle withdrawn completely. The inlet end 16 of the column 14 should then immediately be inserted into the chromatograph oven 12 by depressing the bracket 22 toward the oven wall. The entire volume of injected sample, which has spread over a finite length of the column, will thus be exposed to the heated environment of the oven at substantially the same time. Such abrupt heating provides uniform volatilization of the sample, resulting in reduced and broadening of the components (i.e., band broadening) as the sample emerges from the opposite end of the column 14.

Although the foregoing invention has been described in some detail by way of illustration and example for purposes of clarity and understanding, it will be obvious that certain changes and modifications may be practiced within the scope of the appended claims.

What is claimed is:

1. An injector for receiving a sample from a syringe needle and introducing said sample into a capillary column in an oven of a gas chromatograph, said injector comprising:
    a syringe holder having a central bore for receiving the syringe needle;
    means located at one end of the central bore for fastening an inlet end of the capillary tube;
    means located at the other end of the central bore for sealing the central bore when the syringe needle is not therein; and
    means for supporting the syringe holder relative to the gas chromatograph, said supporting means being collapsible so that the distance between the syringe and the oven can be abruptly varied to withdraw a portion of the capillary column from the oven.

2. An injector as in claim 1, wherein the supporting means comprises a baseplate fixed to the chromatograph oven and a telescopic column extending between the baseplate and the syringe holder.

3. An injector as in claim 1, wherein the syringe holder includes an inlet port communicating with the central bore for introducing a carrier gas into the capillary column and a purge port communicating with the central bore for bleeding at least a portion of the carrier gas before it can enter the capillary column.

4. An injector as in claim 1, wherein the sealing means is a stop cock.

5. An on-column injector for a gas chromatographic system having an oven and a capillary column within the oven, wherein the injector includes means for receiving a syringe needle and guiding the needle to an inlet end of said capillary column, said injector characterized by means for collapsibly mounting the injector so that said inlet end may be removed from the oven during injection of a sample from the syringe needle and inserted into the oven after the sample injection is completed.

6. An on-column injector as in claim 5, wherein the means for collapsibly mounting the injector comprises a telescopic column support.

7. A method for introducing a sample into a capillary column located within the oven of a gas chromatograph, said method comprising:
   maintaining an initial portion of the column outside of the oven;
   continuously flowing a carrier gas through the column;
   injecting the sample into the initial portion of the column; and
   abruptly inserting the intitial portion of the column into the oven.

8. A method as in claim 7, wherein the sample volume is less than 1 $\mu$l and the sample is injected into the column over a period of less than 1 second.

9. A method as in claim 7, wherein the sample volume is in the range from 1 to 2 $\mu$l and the sample is injected into the column over a period of from 1 to 5 seconds.

10. A method as in claim 7, wherein the sample volume is over 2 $\mu$l and the sample is injected into the column over a period of from 5 to 10 seconds.

* * * * *